United States Patent
Ibrahim

(10) Patent No.: US 7,623,827 B2
(45) Date of Patent: Nov. 24, 2009

(54) VOLTAGE OVERSHOOT PROTECTION

(75) Inventor: Ibrahim Ibrahim, North Ryde (AU)

(73) Assignee: Cochlear Limited, Lane Cove (AT)

( * ) Notice: Subject to any disclaimer, the term of this patent is extended or adjusted under 35 U.S.C. 154(b) by 883 days.

(21) Appl. No.: 10/968,001

(22) Filed: Oct. 20, 2004

(65) Prior Publication Data

US 2008/0195177 A1 Aug. 14, 2008

(30) Foreign Application Priority Data

Oct. 20, 2003 (AU) ............................. 2003905729

(51) Int. Cl.
H04B 5/00 (2006.01)
(52) U.S. Cl. .................... 455/41.1; 455/42; 455/77; 455/102; 340/10.3; 340/10.4; 340/10.5; 607/32; 607/33; 607/60
(58) Field of Classification Search .............. 455/41.1, 455/41.2, 42, 77, 102, 108; 340/10.3, 10.4, 340/10.5, 10.2, 825.72, 825.77; 607/32, 607/33, 60, 61
See application file for complete search history.

(56) References Cited

U.S. PATENT DOCUMENTS

| 7,079,901 B1 * | 7/2006 | Loftin et al. ................... 607/60 |
| 2002/0032471 A1 | 3/2002 | Loftin et al. |
| 2005/0283207 A1 * | 12/2005 | Hochmair et al. ............. 607/55 |

OTHER PUBLICATIONS

Australian Application 2004222765- First Examiner's Report dated Feb. 13, 2009.

* cited by examiner

*Primary Examiner*—Tuan A Pham
(74) *Attorney, Agent, or Firm*—Connolly Bove Lodge & Hutz LLP

(57) ABSTRACT

A transmission circuit for an RF inductive link, particularly for an implanted device such as a cochlear implant. In a preferred form, the transmission circuit 1 includes a transmitter coil 24 and a damping device, including an auxiliary coil 4 and switch 6. The switch is operated to close the coil circuit when data zeros are transmitted. This has the advantage of improving modulation depth without placing stress on the RF driver output switches.

14 Claims, 8 Drawing Sheets

(PART I)

(PART II)

(PART I)

(PART II)

(PART I)

(PART II)

(PART I)

(PART II)

VOLTAGE OVERSHOOT PROTECTION

CROSS-REFERENCE TO RELATED APPLICATIONS

This application claims priority from Australian Provisional Patent Application No. 2003905729 filed on Oct. 20, 2003, the contents of which is incorporated herein by reference.

BACKGROUND

1. Field of the Invention

The present invention relates to inductive data links, and particularly but not exclusively to data links and transmission protocols that are used in conjunction with implantable medical devices.

2. Related Art

Inductive links are used in many applications, but have particular application to implanted medical devices such as pacers, cochlear implants and other neural stimulators, and other types of devices. They allow for data and/or power to be transmitted to a device which is wholly implanted from an external system, without requiring a cable or connection to pass through the skin.

Hearing aids and cochlear implants are useful in restoring the sensation of hearing to hearing impaired individuals. This is an area where inductive links are widely applied.

A cochlear implant is used where the hair cells of the cochlea have been damaged to the extent that they are no longer able to convert the mechanical vibration of the cochlea fluid into an electrical signal. The cochlear implant generally bypasses the hair cells of the cochlea and delivers electrical stimulation, representative of speech and environmental sounds, to the nerves in the cochlear. The neural impulses generated by the electrical stimulation are then sent to the brain, thereby allowing the brain to perceive a hearing sensation.

The functional components of a cochlear implant system typically include an external sound processor device connected to an external headset/transmitter coil, and an implanted receiver-stimulator connected to an implanted electrode array.

In operation, the sound processor device detects sound and converts this into a binary coded, serial data stream, representative of the desired stimulation parameters. The serial data stream then modulates a high frequency (RF) analogue carrier. Typically, the serial data stream is 100% amplitude modulated on the analogue carrier, for example as is described in U.S. Pat. No. 4,532,930 ("Crosby") or U.S. Pat. No. 5,741,314 ("Daly"). The contents of these documents are incorporated herein by reference.

The modulated signal is then output from a number of RF output driver circuits in the speech processing device, and sent to the headset/transmitter coil.

The headset/transmitter coil is frequency-tuned as a series resonance circuit that is inductively linked with a parallel-tuned resonant circuit in the form of the receiver coil in the receiver-stimulator. A voltage waveform thus induced in the receiver coil has a voltage waveform envelope representing the serial data steam.

A problem with such inductive communication links is that errors can occur when the modulation depth of the waveform received in the receiver coil falls below a certain threshold.

The modulation depth of the received waveform depends on a number of factors.

One factor is the tuned frequency and quality factor of the transmitter and receiver coils, since the higher the effective quality factor, the lower the modulation depth of the received waveform and the longer the after-burst ringing in both the transmitted and the received waveforms.

Another factor is the effective coupling coefficient between the transmitter and receiver coils. The modulation depth of the received waveform decreases with an increased distance between the two coils.

The prior art has employed a 'tri-state' function to reduce such data errors. Basically, this involves open-circuiting the output switches of the RF drivers during transmission of data "zeros", inter-phase gaps and/or inter-frame gaps. Conversely, the output switches of the RF drivers are close-circuited during transmission of data "ones". This 'tri-state' function reduces the effective quality factor of the transmitter coil, increases the resonance frequency, thus creating a higher frequency post RF-burst ringing that decays quickly. The interaction of the transmitted signal with the receiver coil leads to a larger modulation depth and thus improved data integrity.

However, a drawback of the prior art tri-state function is that an excessive voltage overshoot is generated when the output switches of the RF drivers are open-circuited. For example, RF switches operating with a supply voltage of 3.3V will produce an RF output voltage swinging between −0.8V and 4.1V, as a result of the output voltage overshoot when the switches are opened. The voltage of the RF drivers exceeds the power supply rails by a forward diode drop, typically about 0.8V above VDD and 0.8V below VSS.

This voltage overshoot can affect the reliability of the integrated circuit since the output switches may be overstressed from being operated outside the maximum operating voltage specified by the integrated circuit manufacturer. Further, this overstressing can gradually weaken, and eventually permanently damage the output switches.

One technique used to reduce the effects of this voltage overshoot is to provide protection diodes at each of the output switches. However, these diodes only share the current during the voltage overshoot and do not affect the voltage by any significant amount. Further, voltage waveform clamping and current conduction through the diodes defeats the purpose of the tri-state function until the signal drops below the clamping point.

It is an object of the present invention to provide an improved RF transmission arrangement for inductive links.

In accordance with one aspect of the present invention, there is provided an RF transmission circuit for transmitting at least a data signal across an inductive link, said transmission circuit comprising:

modulation means for modulating a high frequency carrier signal with the data signal to provide an output signal; and transmission means, including a transmission coil, for transmitting the output signal across the inductive link, wherein said transmission means includes an output signal damping means that is selectively operable according to the value of the data signal.

Preferably, the RF damping means operates to increase the tuned frequency of the transmission coil and more preferably, the damping means includes an auxiliary coil closely coupled to the transmission coil.

Preferably, the modulating means provides amplitude modulation and preferably the amplitude modulation is substantially 100% modulation and the data signal is a serial digital data stream.

SUMMARY

In accordance with another aspect of the present invention, there is provided a RF transmission circuit for a cochlear implant system, said transmission circuit including:

modulating means for modulating a high frequency carrier signal with a serial data stream for transmission to an implanted stimulation device;

a headset coil for transmitting an output signal from said modulating means across a transcutaneous inductive link for detection by an implanted receiver coil;

wherein said circuit further includes a damping means that is selectively operable according to a momentary value of the serial data stream.

In accordance with another aspect of the present invention, there is provided a method of transmitting a stream of binary data across an inductive link, said method comprising the steps of:

modulating a high frequency carrier signal with the data to provide an output signal; and transmitting said output signal across the inductive link;

wherein said transmitting step includes the sub-step of selectively damping said high frequency carrier signal according to a momentary value of the binary data.

The present invention avoids the voltage overshoot problem of the prior art Tri-State approach by utilising a damping arrangement, so as to provide the desired improved modulation depth in the received waveform. This selectively increases the tuned frequency of the transmitter coil to provide fast decay of ringing in the receiver coil. In a preferred form, the damping is provided by a closely coupled auxiliary coil, operated when the momentary state of the data is a zero.

BRIEF DESCRIPTION OF THE DRAWINGS

A preferred form of the present invention will now be described by way of example with reference to the accompanying drawings, in which.

DETAILED DESCRIPTION

It will be appreciated that whilst present invention will be principally described with reference to cochlear implants, the principles of the present invention may be applied in relation to many other types of inductive links, and in particular to other types of implanted medical devices. It is applicable whether or not power and data, or data alone, are being transmitted. It is also applicable whether the link operates more or less continuously, or in a more sporadic or occasional mode.

Before describing the features of one implementation of the present invention in detail, it is convenient to further describe the construction and overall operation of one example of a cochlear implant system. It will be understood that the present invention could be applied to other types of cochlear implants.

Figure 1:
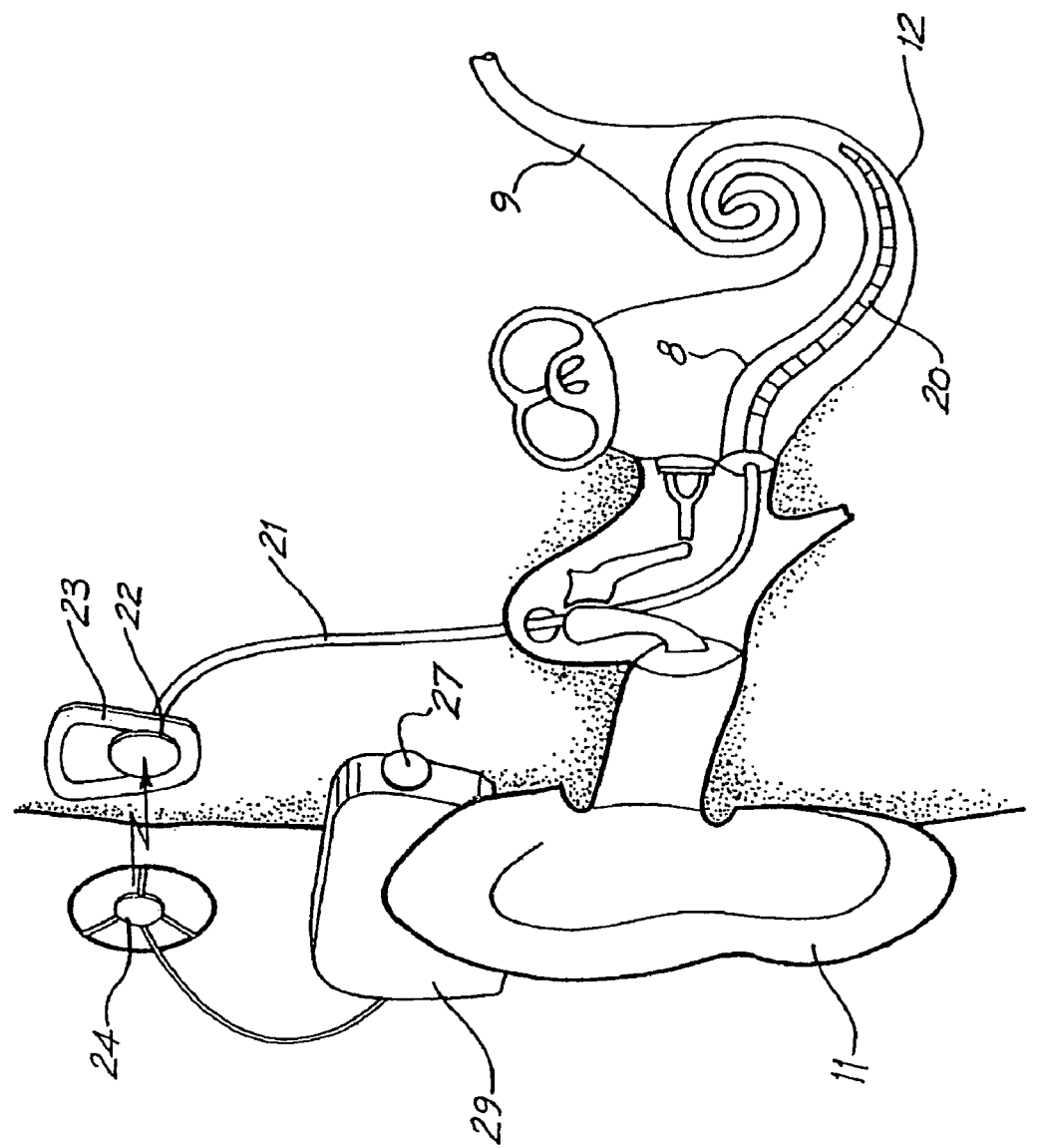
FIG. 1 is an illustrative diagram showing a general arrangement of a cochlear implant system.

Referring to FIG. 1, the external sound processor device 29 includes an on-board microphone 27 and is generally configured to fit behind the outer ear 11, as shown. The sound processor device 29 is connected to a headset transmitter coil 24 which transmits power and data signals to the implanted receiver-stimulator unit 22 over a transcutaneous RF link.

The signals transmitted by the headset coil 24 are received by a receiver coil 23 in the receiver-stimulator unit 22 and then applied to the electrode array 20. The electrode array 20 applies electrical stimulation signals to the basilar membrane 8, to thereby stimulate the auditory nerve 9. The electrical stimulation signals are normally bi-phasic and charge balanced to ensure there is no net DC current flow.

It is noted that the receiver coil 23 can also transmit signals back to the headset coil 24 for telemetry purposes, as described for example in U.S. Pat. No. 5,758,651, the contents of which are incorporated herein by reference.

Figure 2A:
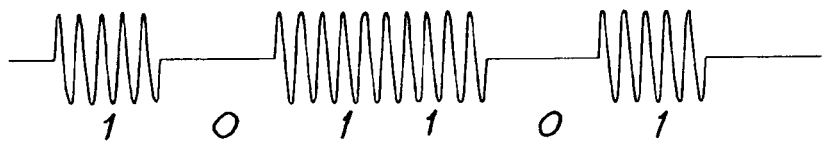
FIGS. 2A to 2C show explanatory example waveforms used to assist in the understanding of this disclosure.

The sound processor device 29 receives sound and calculates a digital data stream, representing the electrical stimulation parameters according to a selected coding strategy. The digital data stream then modulates a radio frequency (RF) carrier which is then inductively transmitted over the transcutaneous link to the receiver coil 23. Typically, the means for modulation performs 100% amplitude modulation and can be combined with pulse width modulation, as shown for example in FIG. 2A.

In this example, the RF signal is transmitted at an average signal frequency of 5 MHz, although the headset transmitter coil 24 and the receiver coil 23 are stagger-tuned to achieve the required bandwidth for the data communication. For example, the headset coil 24 is tuned to 4.8 MHz in a high quality-factor, series resonance circuit and the receiver coil 23 is tuned to 5.2 MHz in a parallel resonance circuit.

Figure 2B:
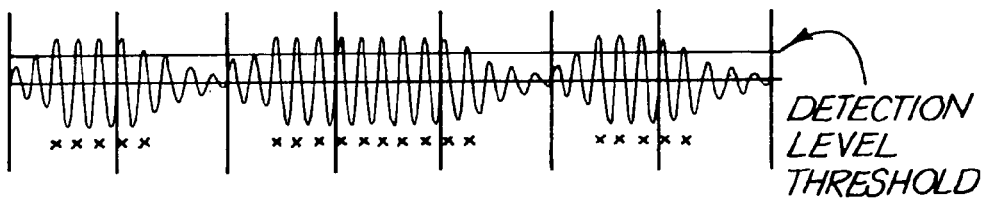
Figure 2C:
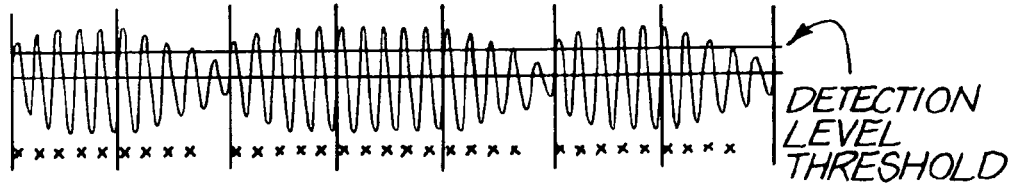

The headset coil 24 and receiver coil 23 are separated by a distance of between approximately 1 mm and 10 mm. FIGS. 2B and 2C show how the waveform received at the receiver coil 23 can vary according to the separation distance between the headset coil 24 and the receiver coil 23.

The voltage waveform across the receiver coil 23 is an amplitude modulated signal whose envelope represents the original serial digital data steam. A typical modulated signal has a series of 5 pulses for a one, and 5 time spaces with no pulses for a zero.

The receiver-stimulator unit 22 receives and decodes the amplitude modulated signal into a stimulation signal which is then applied to the electrode array 20. The incoming signal is also rectified to generate an internal power supply.

Figure 4:
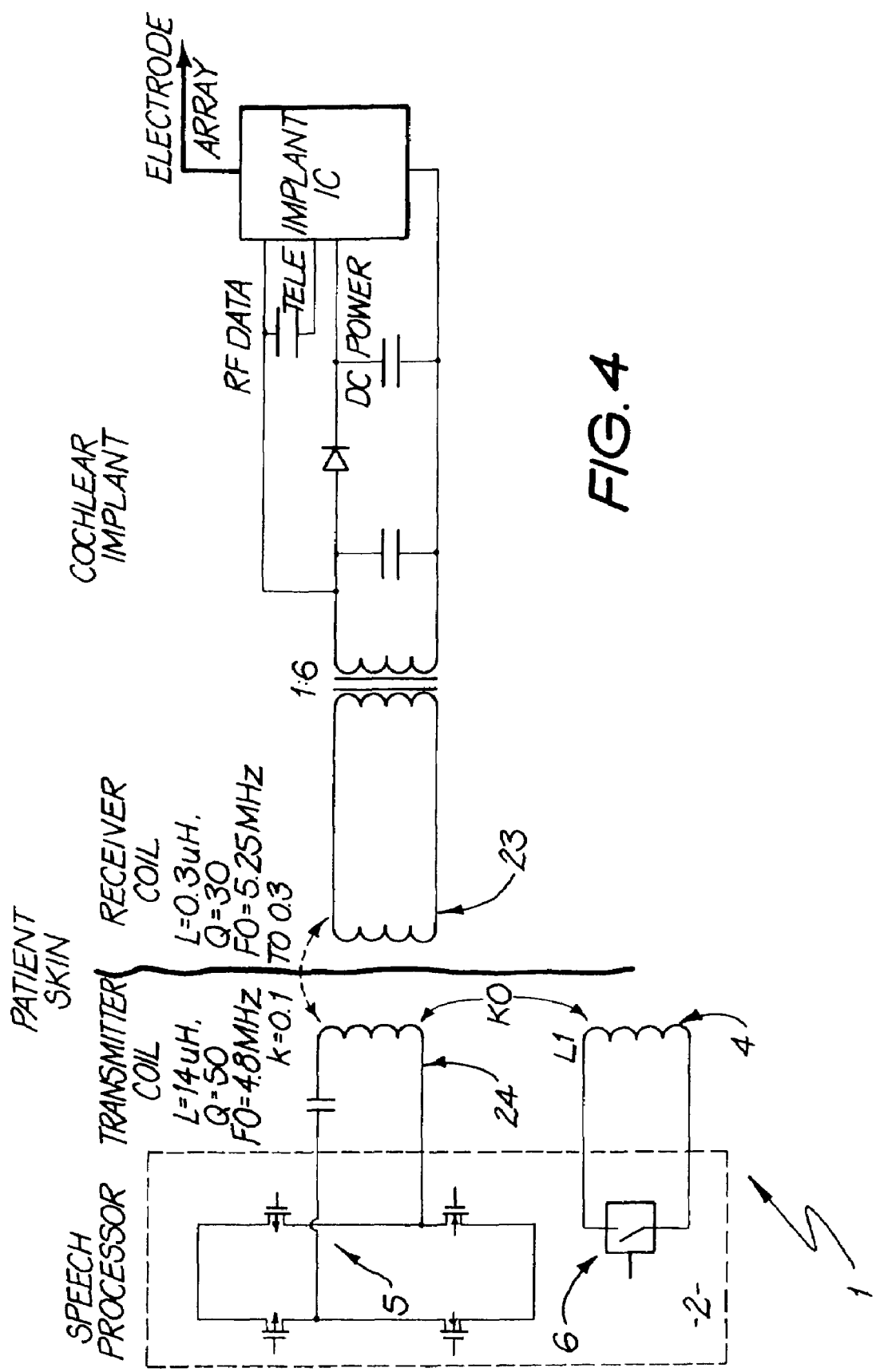
FIG. 4 is a schematic diagram of a transmitter circuit according to this disclosure.

Referring now to FIG. 4, an example of a transmitter circuit 1 according to the present disclosure will be described.

The transmitter circuit 1 includes the headset transmitter coil 24 as described above, an RF driver circuit 2 and an auxiliary coil 4. The RF driver circuit 2, which is normally provided as an integrated circuit, includes a number of H-bridge RF output driver switches 5 and a low impedance switch 6 connected to the auxiliary coil 4. Preferably, the auxiliary coil 4 has a single turn and is provided on a printed circuit board (PCB) in common with the transmitter coil 24.

It is preferred that the auxiliary coil 4 is physically located in close proximity to the transmitter coil 24, and is dimensioned so as to have as high a coupling co-efficient with the transmitter coil 24 as possible. It may conveniently be located within the headset with the transmitter coil.

In operation, when the transmitter coil 24 transmits a data "1", the low impedance switch 6 is open circuited, and thereby inhibits current flow through the auxiliary coil 4.

Conversely, when the transmitter coil 24 transmits a data "0", the low impedance switch 6 is closed and the auxiliary coil 4 is short-circuited. The low impedance switch 6 is also closed during inter-phase gaps and inter-frame gaps.

The switching may be controlled by detection of data zeros in the data stream. Alternatively, a separate signal could be sent by the speech processor to control switching.

When the auxiliary coil 4 is short-circuited, its inductance is reflected as a high capacitive impedance, in series with the transmitter coil 24. This causes a large increase in the tuned frequency of the transmitter coil 24, which when combined with the losses of the auxiliary coil 4 and the low impedance switch 6, leads to fast decay or damping of the post RF-burst ringing waveform. In effect, the effective inductance of the transmitter circuit is increased. A fast decay of the ringing waveform improves the modulation depth and hence reliability of the data signal against errors, as earlier discussed. The RF driver switches 5 can operate normally, without subjecting them to excessive voltage overshoots.

The low impedance switch 6 is controlled by a signal that causes the switch 6 to close according to the data signal. Accordingly, the switch 6 is closed when the momentary value is binary zero, during interphase gaps and during interframe gaps.

Figure 3:
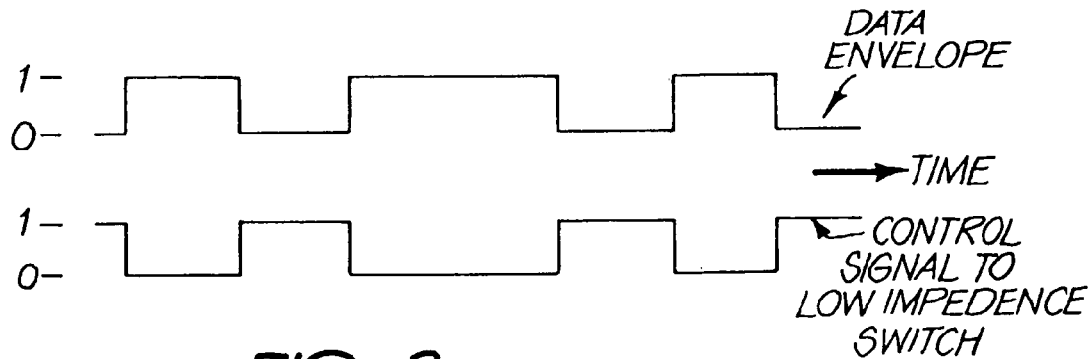
FIG. 3 is a further explanatory example waveform.

An example of a digital serial data stream is shown as the upper waveform in FIG. 3, whereas the lower waveform of FIG. 3 shows a control signal applied to the low impedance switch 6.

The coupling coefficient KO between the transmitter coil 24 and the auxiliary coil 4 is usually set to a high value, for example, greater than 70%. The inductance of the auxiliary coil 4 is designed so that the peak voltage induced across the auxiliary coil 4 cannot exceed one diode drop above VDD, to avoid signal clamping.

It can be seen that the transmitter circuit 1 thus provides signal damping without causing excessive voltage stress on the RF output switches 5, as is the case with the earlier tri-state function. The integrated circuit can be protected against voltage overshoot of the resonance circuit associated with the transmitter coil 24, without compromising the data integrity of the RF link.

The RF output remains connected to either VDD or VSS, depending on the circuit design and the polarity of the input clock, as will be understood by the person skilled in the art.

FIGS. 5A to 5F show a series of waveforms demonstrating test results of the transmission circuit 1 according to this disclosure, in comparison with prior art, tri-stating techniques.

Figure 5A:
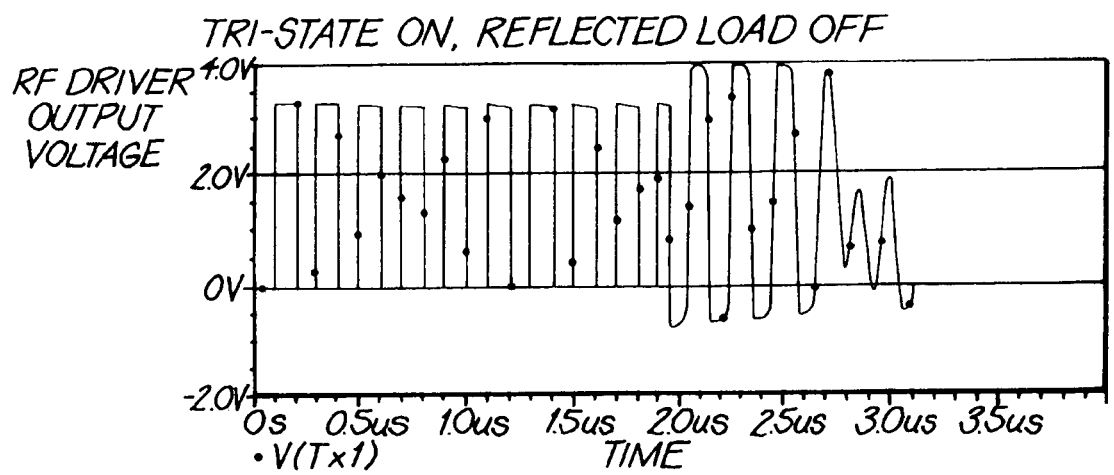
FIGS. 5A to 5F show a series of comparative waveforms used to assist in the understanding of this disclosure.
Figure 5A:
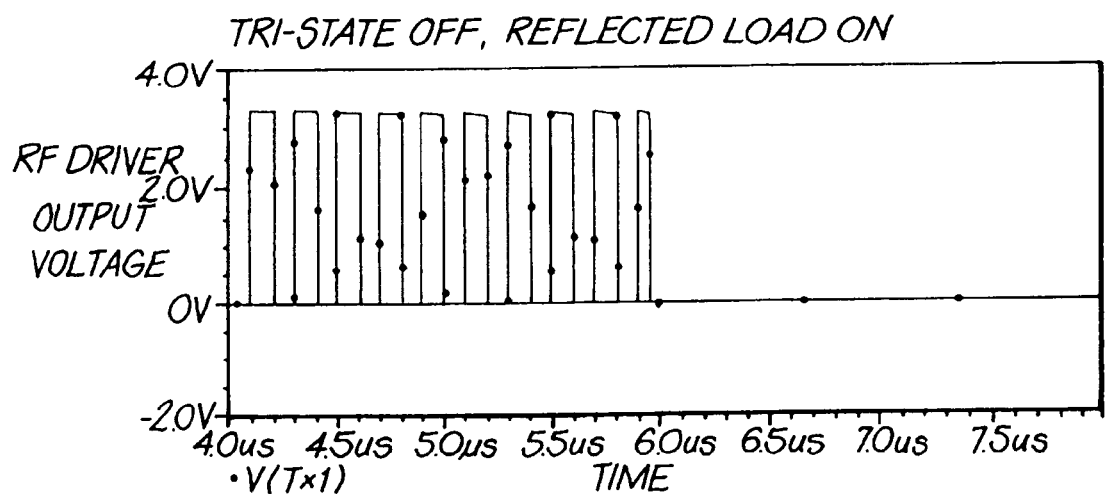

FIG. 5A labelled "RF Driver output voltage" shows two waveforms, side by side. The waveform of the left hand side of FIG. 5A shows a voltage overshoot associated with the prior art tri-state function, when the RF output driver is open circuited after 2.0 µs. In contrast, the waveform on the right hand side of FIG. 5A does not have the same voltage overshoot because a reflected load is applied in accordance with this disclosure, after 2.0 µs.

Figure 5B:
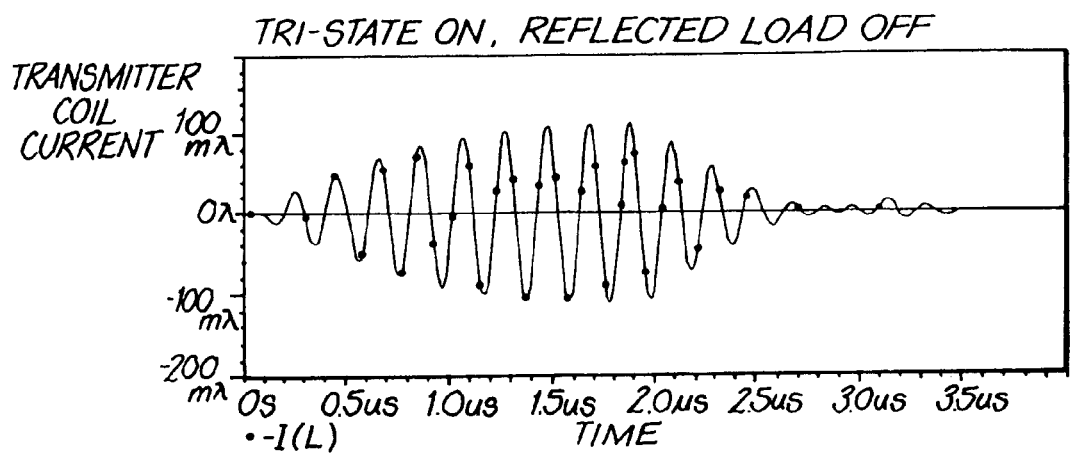
Figure 5B:
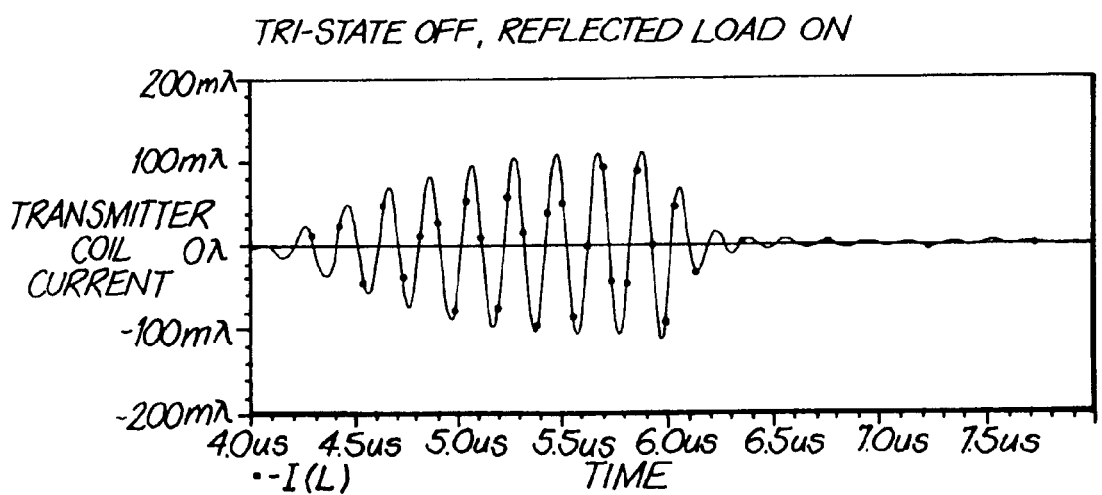

Similarly, FIG. 5B labelled "Transmitter coil current" shows on the right hand side how an absence of voltage overshoot reduces the number of ringing cycles during a zero data interval.

Figure 5C:
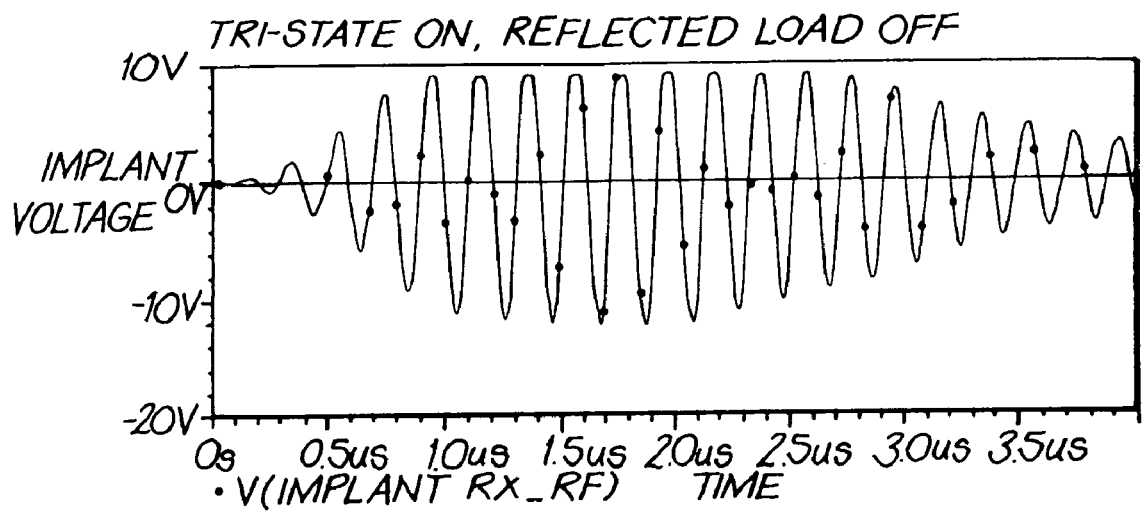
Figure 5C:
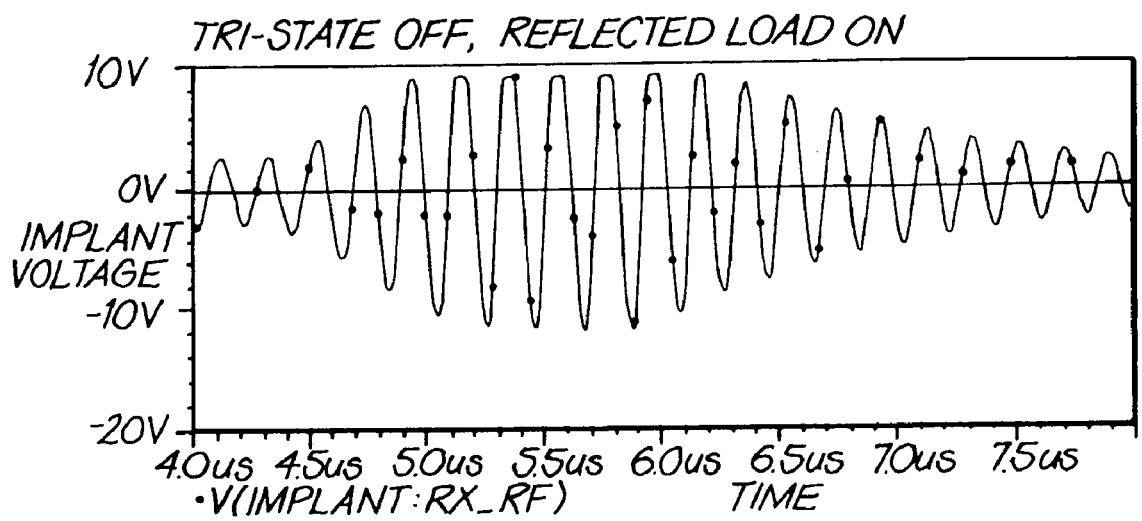
Figure 5D:
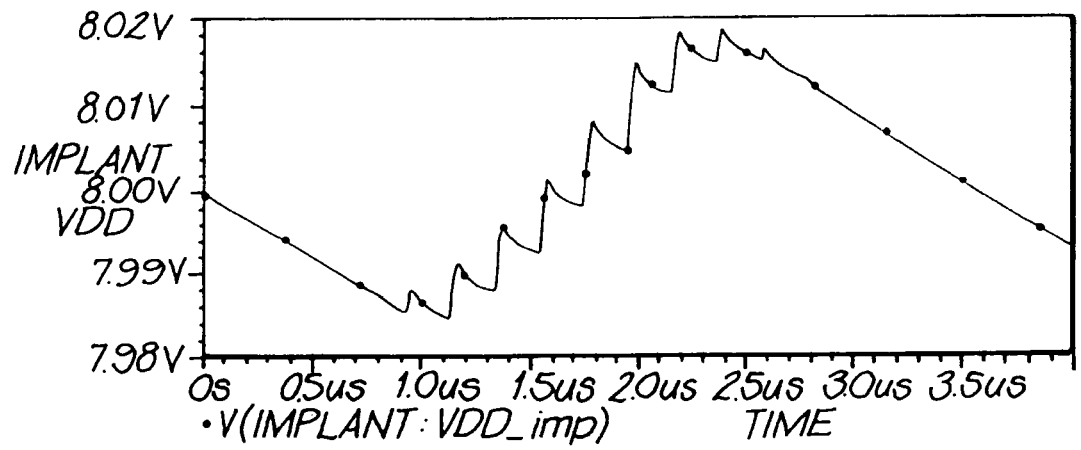
Figure 5D:
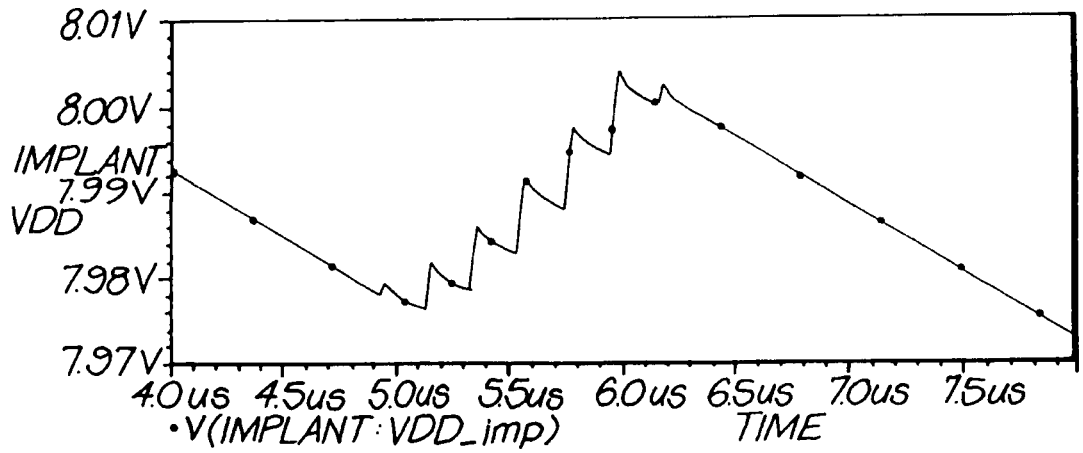

FIGS. 5C and 5D also show comparative waveforms for the implant voltage and implant VDD, respectively.

Figure 5E:
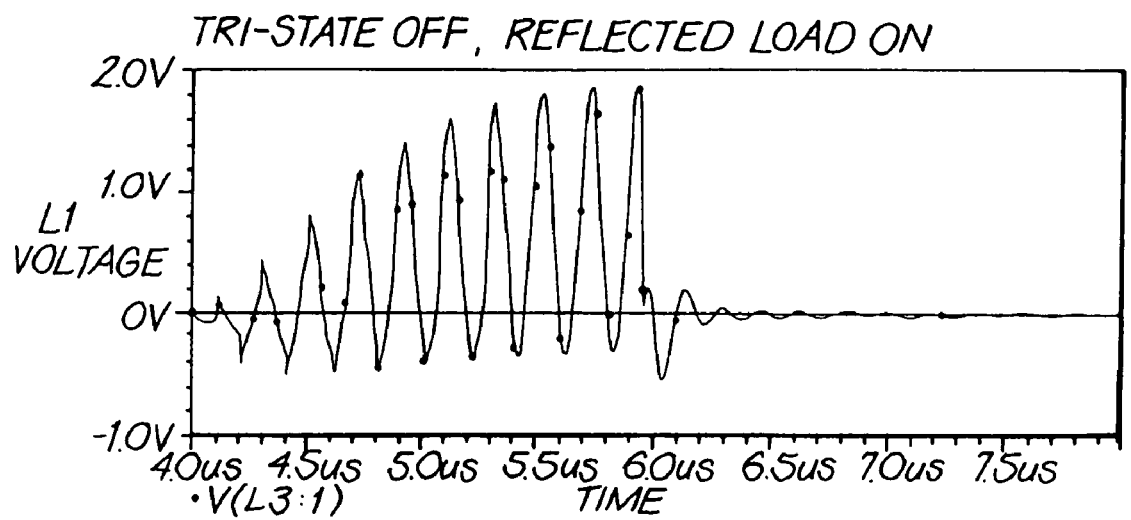
Figure 5F:
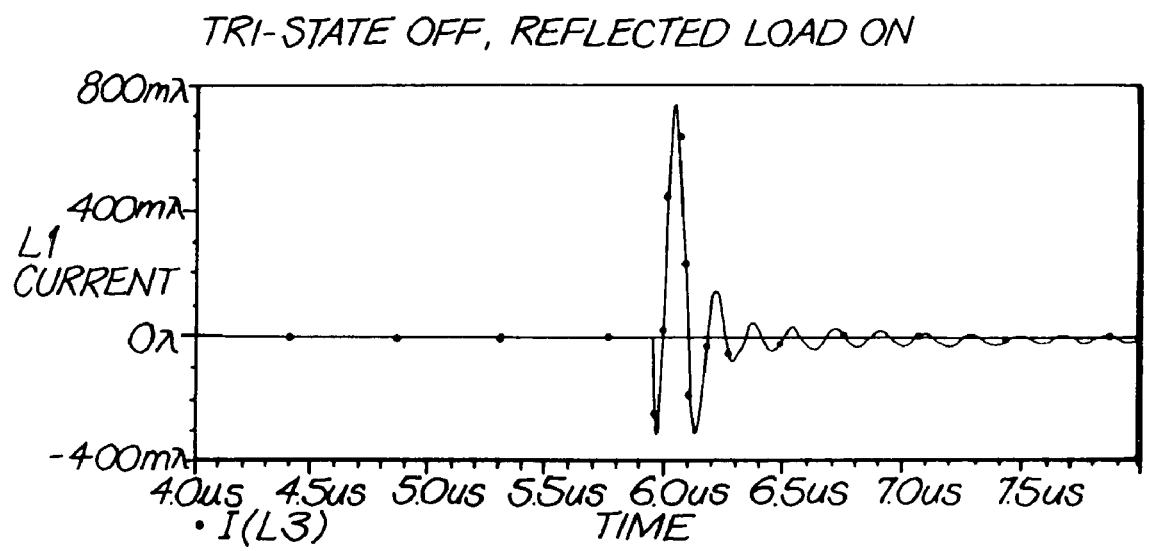

FIGS. 5E and 5F show the current waveforms in the transmitter coil 24 and auxiliary coil 4 respectively. The switch is operated just before time 6.0 microseconds on each graph, and shows the rapid decay of ringing in the transmitter coil.

Although the present invention has been described with reference to a particular embodiment, it is to be understood that this embodiment is merely illustrative of the application of the principles of the invention. Thus numerous modifications may be made as will be understood by those skilled in the art, without departing from the principles of the invention.

What is claimed is:

1. An RF transmission circuit for transmitting at least a data signal across an inductive link, said transmission circuit comprising:
   modulation means for modulating a high frequency carrier signal with the data signal to provide an output signal; and
   transmission means, including a transmission coil, for transmitting the output signal across the inductive link, wherein said transmission means includes an output signal damping means that is selectively operable according to the value of the data signal, wherein the damping means comprises:
   an auxiliary coil; and
   a switch in parallel with the auxiliary coil; and
   wherein RF transmission circuit is configured to open the switch in response to the value of the data signal being equal to a first value and close the switch in response to the value of the data signal being equal to a second value.

2. The RF transmission circuit of claim 1, wherein said damping means operates to increase the tuned frequency of the transmission coil.

3. The RF transmission circuit of claim 2, wherein damping means includes an auxiliary coil.

4. The RF transmission circuit according to claim 1, wherein said modulating means provides amplitude modulation.

5. The RF transmission circuit of claim 4, wherein said amplitude modulation is substantially 100% modulation and the data signal is a serial digital data stream.

6. The RF transmission circuit according to claim 5, wherein said damping means is configured to operate at least when a state of the data signal is digital zero.

7. The RF transmission circuit according to claim 3, wherein the auxiliary coil is closely coupled to the transmission coil.

8. An RF transmission circuit for a cochlear implant system, said transmission circuit comprising:
   modulating means for modulating a high frequency carrier signal with a serial data stream for transmission to an implanted stimulation device; and
   a headset coil for transmitting an output signal from said modulating means across a transcutaneous inductive link for detection by an implanted receiver coil;
   wherein said circuit further comprises a damping means that is selectively operable according to a momentary value of the serial data stream; and
   wherein the damping means comprises:
   an auxiliary coil; and
   a switch in parallel with the auxiliary coil; and
   wherein RF transmission circuit is configured to open the switch in response to the value of the data signal being equal to a first value and close the switch in response to the value of the data signal being equal to a second value.

9. The RF transmission circuit of claim 8, wherein said damping means comprises an auxiliary coil magnetically coupled to said headset coil, said damping means permitting current flow through said auxiliary coil when said damping means is operated.

10. The RF transmission circuit of claim 9, wherein said damping means is operated when the serial data stream has a momentary value of zero.

11. The RF transmission circuit of claim 9, wherein said damping means comprises a switching circuit arranged on an integrated circuit together with said modulating means.

12. A method of transmitting a stream of binary data across an inductive link, said method comprising the steps of:
modulating a high frequency carrier signal with the data to provide an output signal; and
transmitting said output signal across the inductive link;
wherein said transmitting step includes the sub-step of selectively damping said high frequency carrier signal according to a momentary value of the binary data;
wherein the sub-step of selectively damping comprises:
opening a switch in response to the value of the data signal being equal to a first value, and
closing the switch in response to the value of the data signal being equal to a second value; and
wherein the switch is in parallel with an auxiliary coil.

13. A method according to claim 12, wherein the damping sub-step includes operating a switch so as to close a circuit including an auxiliary coil.

14. A method according to claim 13, wherein the damping sub-step is selected when the momentary value of the data is zero.

* * * * *